United States Patent [19]

Leone-Bay et al.

[11] Patent Number: 4,568,380
[45] Date of Patent: Feb. 4, 1986

[54] HERBICIDAL ESTERS OF 2-BROMO-4-METHYLIMIDAZOLE-5-CARBOXYLIC ACID

[75] Inventors: Andrea Leone-Bay, Ridgefield, Conn.; Peter E. Timony, Valley Cottage, N.Y.

[73] Assignee: Stauffer Chemical Company, Westport, Conn.

[21] Appl. No.: 662,000

[22] Filed: Oct. 18, 1984

[51] Int. Cl.$^4$ ................ A01N 43/50; C07D 403/06
[52] U.S. Cl. .................... 71/92; 260/245.6; 546/210; 548/336; 548/337
[58] Field of Search ............. 548/337, 336; 546/210; 260/245.6; 71/92

[56] References Cited

U.S. PATENT DOCUMENTS 4,340,598 7/1982 Furukawa et al. ............ 548/337 X

*Primary Examiner*—Richard A. Schwartz
*Attorney, Agent, or Firm*—Edwin H. Baker

[57] ABSTRACT

A herbicidal compound having the structural formula

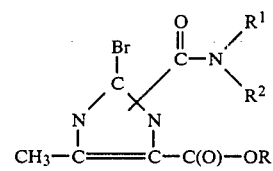

wherein R is $C_1$–$C_{10}$ alkyl, $C_3$–$C_8$ cycloalkyl, $C_3$–$C_8$ cycloalkylalkyl wherein the alkyl has 1 to 6 carbon atoms, $C_3$–$C_{10}$ alkenyl, $C_5$–$C_8$ cycloalkenyl; benzyl or mono- or di-substituted benzyl wherein the substituents are $C_1$–$C_4$ alkyl, halogen, nitro or $C_1$–$C_4$ haloalkyl; $R^1$ and $R^2$ independently are $C_1$–$C_6$ alkyl or aryl, or $R^1$ and $R^2$ together form a ring with the nitrogen to which they are attached having 3–8 carbon atoms, optionally substituted with one or two methyl groups.

14 Claims, No Drawings

HERBICIDAL ESTERS OF 2-BROMO-4-METHYLIMIDAZOLE-5-CARBOXYLIC ACID

BACKGROUND OF THE INVENTION

Compounds having the structural formula

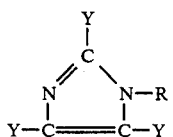

wherein R is hydrogen, alkyl or substituted alkyl and Y is hydrogen, alkyl, substituted alkyl, halogen, cyano or nitro are described in U.S. Pat. No. 3,501,286 as being herbicides.

A compound of the formula

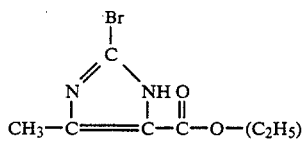

is taught by Pyman and Timmis, *J. Chem. Soc.*, pp. 494–498 (1923). However, no utility for this compound is taught other than its use as an intermediate in the preparation of pharmaceuticals.

DESCRIPTION OF THE INVENTION

This invention relates to esters of 2-bromo-4-methylimidazole-5-carboxylic acid as herbicides. The novel compounds of this invention have the following structural formula (A)

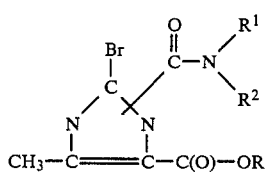

wherein R is $C_1$-$C_{10}$ alkyl, preferably $C_3$-$C_6$ alkyl, more preferably $C_3$-$C_5$ alkyl, most preferably isopropyl, isobutyl, isopentyl, or sec-pentyl; $C_3$-$C_8$ cycloalkyl, preferably $C_4$-$C_6$ cycloalkyl, more preferably cyclopentyl or cyclohexyl; $C_3$-$C_8$ cycloalkylalkyl wherein the alkyl has 1 to 6 carbon atoms, preferably cyclopropylmethyl or cyclopentylmethyl; $C_3$-$C_{10}$ alkenyl, preferably allyl or 2-methyl-3-butenyl-1; $C_5$-$C_8$ cycloalkenylbenzyl or mono- or di-substituted benzyl wherein the substituents are $C_1$-$C_4$ alkyl, halogen, nitro or $C_1$-$C_4$ haloalkyl; $R^1$ and $R^2$ independently are $C_1$-$C_6$ alkyl, preferably $C_1$-$C_4$ alkyl, aryl, preferably phenyl; or $R^1$ and $R^2$ together form a ring with the nitrogen to which they are attached, having 3–8 carbon atoms, optionally substituted with one or two methyl groups. Suitable compounds within the above genus are those wherein R is $C_3$-$C_5$ alkyl, $R^1$ is $C_1$-$C_4$ alkyl and $R^2$ is $C_1$-$C_4$ alkyl.

Structural formula A is intended to define compounds of either of the following two structural isomers:

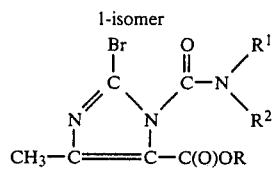

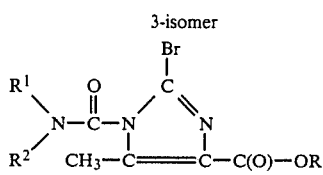

or mixtures of the two isomers in any proportion.

Both isomers are herbicidally active.

In the above description of the compounds of this invention alkyl includes both straight and branched configurations; for example, methyl, ethyl, n-propyl, isopropyl, n-butyl, sec-butyl, isobutyl, and tert-butyl, the amyls, the hexyls, the heptyls, the nonyls and the decyls.

The compounds of this invention ae active herbicides of a general type. That is, they are herbicidally effective against a wide range of plant species. The method of controlling undesirable vegetation of the present invention comprises applying an herbicidally effective amount of the above-described compounds to the area where control is desired.

The compounds of the present invention can be prepared by the following general method.

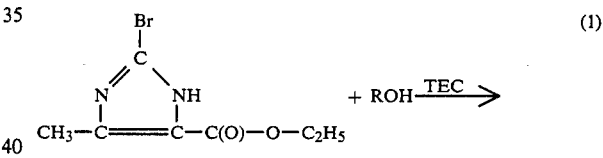

(1)

wherein R is as defined. and TEC is a transesterification catalyst such as Ti(O-alkyl)$_4$, preferably Ti(isopropoxy)$_4$.

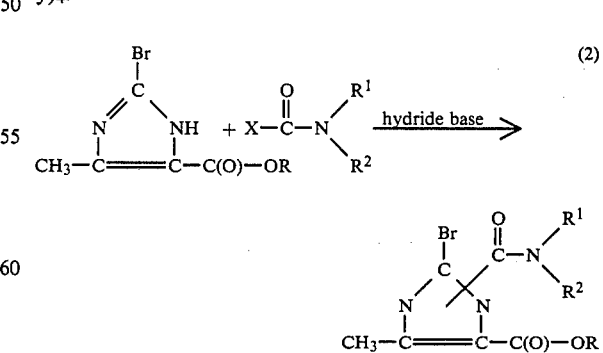

(2)

wherein R, $R^1$ and $R^2$ are as defined, and X is chlorine.

Generally, for step (1) at least one mole of the alcohol is used for the reaction with the ethyl ester to prepare the imidazoles. Preferably, a slight mole excess of the alcohol is used. The reaction mixture is refluxed until completion of the reaction. The reaction product is recovered by removing the volatile materials. Atmospheric, subatmospheric or superatmospheric pressures can be used, depending on the boiling point of the solvent used. Ethanol is conveniently stripped at elevated temperatures and reduced pressure.

Reaction step (2) is run in a solvent such as tetrahydrofuran, at a temperature of about 25°, preferably room temperature, using equal mole amounts of the two reactants and a hydride base. Preferably, the hydride base is sodium hydride.

The reaction product is a mixture of (1) and (3) isomers and is worked up by conventional techniques.

The following example teaches the synthesis of a representative compound of this invention.

EXAMPLE I

Isopropyl ester of 2-Bromo-4-methyl-5-imidazolecarboxylic acid

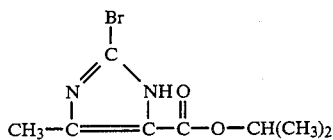

To a suspension of 6.4 grams (g) ($2.7 \times 10^{-2}$ moles) of ethyl-2-bromo-4-methyl-5-imidazole carboxylate in 70 milliliters (ml) of isopropanol was added 0.6 ml ($2.4 \times 10^{-3}$ moles) tetraisopropyl titanate. The resulting mixture was heated to reflux for 3 days, then concentrated in vacuo to one-half the original volume. The solution was cooled on ice and the precipitated crystalline solid was filtered and air dried to give 3.5 g of the desired product, m.p. 193°–194° C.

EXAMPLE II

Ethyl Ester of 1- and 3-N,N-dimethylformamyl-2-bromo-4-methyl-5-imidazolecarboxylic acid

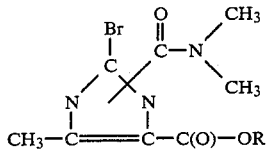

To a suspension of 257 milligrams (mg) ($1.07 \times 10^{-2}$ moles) of sodium hydride in 20 ml of anhydrous tetrahydrofuran was added, in portions, 2.0 g ($8.58 \times 10^{-3}$ moles) of ethyl ester of 2-bromo-4-methyl-5-imidazolecarboxylate. The resulting suspension was cooled to 0° C. and 866 ml ($8.58 \times 10^{-3}$ moles) of dimethylcarbamyl chloride was added by drop. The reaction mixture was stirred overnight at room temperature. The precipitated sodium chloride was removed by filtration and concentration of the filtrate in vacuo gave 2.4 g (96%) of the desired products, ethyl ester of 1- and 3-N,N-dimethylformamyl-2-bromo-4-methyl-5-imidazolecarboxylic acid as a yellow oil.

The following is a table of certain selected compounds that are preparable according to the procedure described herein. Compound numbers assigned to each compound are used throughout the remainder of the application.

TABLE I

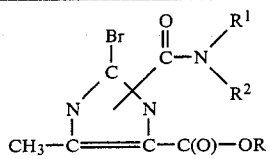

| Compound Number | R | $R^1$ | $R^2$ | $n_D^{25}$ or m.p. °C. |
|---|---|---|---|---|
| 1 | ethyl | ethyl | ethyl | yellow oil |
| 2[a] | ethyl | methyl | methyl | yellow oil |
| 3 | isopropyl | methyl | methyl | colorless oil |
| 4 | isopropyl | isobutyl | isobutyl | colorless oil |
| 5 | isopropyl | butylene | | colorless oil |
| 6 | isopropyl | ethyl | ethyl | yellowless oil |
| 7 | isopropyl | methyl | phenyl | yellowless oil |

[a] Prepared in Example II.

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test. On the day preceding treatment, seeds of eight different weed species are planted in loamy sand soil in individual rows using one species per row across the width of a flat. The seeds used are green foxtail (FT) (*Setaria viridis*), watergrass (WG) (*Echinochloa crusgalli*), wild oat (WO) (*Avena fatua*), annual morningglory (AMG) (*Ipomoea lacunosa*), velvetleaf (VL) (*Abutilon theophrasti*), Indian mustard (MD) (*Brassica juncea*), curly dock (CD) (*Rumex crispus*), and yellow nutsedge (YNG) (*Cyperus esculentus*). Ample seeds are planted to give about 20 to 40 seedlings per row, after emergence, depending upon the size of the plants.

Using an analytical balance, 600 milligrams (mg) of the compound to be tested are weighed out on a piece of glassine weighing paper. The paper and compound are placed in a 60 milliliter (ml) wide-mouth clear bottle and dissolved in 45 ml of acetone or substituted solvent. Eighteen ml of this solution are transferred to a 60 ml wide-mouth clear bottle and diluted with 22 ml of a water and acetone mixture (19:1) containing enough polyoxyethylene sorbitan monolaurate emulsifier to give a final solution of 0.5% (v/v). The solution is then sprayed on a seeded flat on a linear spray table calibrated to deliver 80 gallons per acre (748 L/ha). The application rate is 4 lb/acre (4.48 Kg/ha).

After treatment, the flats are placed in the greenhouse at a temperature of 70° to 80° F. and watered by sprinkling. Two weeks after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

TABLE II

| | Pre-Emergence Herbicidal Activity Application Rate-4.48 kg/ha | | | | | | | |
|---|---|---|---|---|---|---|---|---|
| Cmpd. No. | FT | WG | WO | AMG | VL | MD | CD | YNG |
| 1 | 0 | 0 | 0 | 0 | 0 | 0 | 0 | 0 |

TABLE II-continued

Pre-Emergence Herbicidal Activity
Application Rate-4.48 kg/ha

| Cmpd. No. | FT | WG | WO | AMG | VL | MD | CD | YNG |
|---|---|---|---|---|---|---|---|---|
| 2 | 0 | 0 | 0 | 0 | 0 | 0 | 0 | 0 |
| 3 | 100 | 90 | 60 | 90 | 100 | 100 | 100 | 0 |
| 4 | 0 | 0 | 20 | 60 | 60 | 40 | 90 | 0 |
| 5 | 90 | 80 | 60 | 80 | 100 | 100 | 100 | 0 |
| 6 | 100 | 100 | 75 | 100 | 100 | 100 | 100 | 0 |
| 7 | 100 | 100 | 50 | 100 | 10 | 100 | 85 | 0 |

Post-Emergence Herbicide Test: This test is conducted in an identical manner to the testing procedure for the pre-emergence herbicide test, except the seeds of the eight different weed species are planted 10–12 days before treatment. Also, watering of the treated flats is confined to the soil surface and not to the foliage of the sprouted plants.

The results of the post-emergence herbicide test are reported in Table III.

TABLE III

Post-Emergence Herbicidal Activity
Application Rate-4.48 kg/ha

| Cmpd. No. | FT | WG | WO | AMG | VL | MD | CD | YNG |
|---|---|---|---|---|---|---|---|---|
| 1 | 80 | 20 | 10 | 20 | 10 | 40 | 90 | 0 |
| 2 | 60 | 40 | 10 | 50 | 60 | 40 | 100 | 0 |
| 3 | 100 | 100 | 100 | 100 | 100 | 100 | 100 | 0 |
| 4 | 90 | 70 | 95 | 100 | 100 | 100 | 90 | 0 |
| 5 | 100 | 100 | 70 | 100 | 100 | 100 | 100 | 0 |
| 6 | 100 | 95 | 100 | 100 | 100 | 100 | 60 | 0 |
| 7 | 100 | 100 | 100 | 100 | 100 | 100 | 100 | — |

— = Not tested.

The compounds of the present invention are useful as herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or the petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers and other herbicides, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof, triazine derivatives, such as 2,4-bis(3-methoxypropylamino)-6-methylthio-s-triazine, 2-chloro-4-ethylamino-6-isopropylamino-s-triazine, and 2-ethylamino-4-isopropyl-amino-6-methyl-mercapto-s-triazine; urea derivatives, such as 3-(3,5-dichlorophenyl)-1,1-dimethylurea and 3-(p-chlorophenyl)-1,1-dimethylurea; and acetamides such as N,N-diallyl-α-chloroacetamide, and the like; benzoic acids such as 3-amino-2,5-dichlorobenzoic acid; thiocarbamates such as S-propyl N,N-dipropylthiocarbamate, S-ethyl N,N-dipropylthiocarbamate, S-ethyl cyclohexylthiocarbamate, S-ethyl hexahydro-1H-azepine-1-carbothioate and the like; anilines such as 4-(methylsulfonyl)-2,6-dinitro-N,N-substituted aniline, 4-trifluoromethyl-2,6-dinitro-N,N-di-n-propyl aniline, 4-trifluoromethyl-2,6-dinitro-N-ethyl-N-butyl aniline, 2-[4-(2,4-dichlorophenoxy)-phenoxy]propanoic acid, 2-[1-(ethoxyimino)butyl]-5-[2-ethylthio)propyl]-3-hydroxy-2-cyclohexene-1-one, (±)-butyl-2-[4-[(5-trifluoromethyl)-2-pyridinyl)oxy]-phenoxy]propanate, sodium 5-[2-chloro-4-(trifluoromethyl)phenoxy]-2-nitrobenzoate, 3-isopropyl-1H-2,1,3-benzothiadiazine-4(3H)-one-2,2-dioxide, and 4-amino-6-tert-butyl-3-(methylthio)-as-triazin-5-(4H)-one or (4-amino-6-(1,1-dimethylethyl)-3-(methylthio)-1,2,4-triazin-5(4H)-one). Fertilizers useful in combination with the active ingredients include, for example, ammonium nitrate, urea and superphosphate. Other useful additaments include materials in which plant organisms take root and grow such as compost, manure, humus, sand, and the like.

We claim:

1. A compound having the structural formula

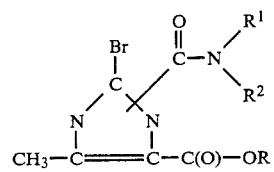

wherein R is $C_1$-$C_{10}$ alkyl, $C_3$-$C_8$ cycloalkyl, $C_3$-$C_8$ cycloalkylalkyl wherein the alkyl has 1 to 6 carbon atoms, $C_3$-$C_{10}$ alkenyl, $C_5$-$C_8$ cycloalkenyl; benzyl or mono- or di-substituted benzyl wherein the substituents are $C_1$-$C_4$ alkyl, halogen, nitro or $C_1$-$C_4$ haloalkyl; $R^1$ and $R^2$ independently are $C_1$-$C_6$ alkyl or phenyl, or $R^1$ and $R^2$ together form a saturated ring with the nitrogen to which they are attached having 3-8 carbon atoms, optionally substituted with one or two methyl groups.

2. The compound of claim 1 wherein R is $C_3$-$C_5$ alkyl, $R^1$ is $C_1$-$C_4$ alkyl and $R^2$ is $C_1$-$C_4$ alkyl.

3. The compound of claim 1 wherein R is isopropyl, $R^1$ is methyl and $R^2$ is methyl.

4. The compound of claim 1 wherein R is isopropyl, $R^1$ is isobutyl and $R^2$ is isobutyl.

5. The compound of claim 1 wherein R is isopropyl, $R^1$ is ethyl and $R^2$ is ethyl.

6. The compound of claim 1 wherein R is isopropyl, and $R^1$ and $R^2$ together are butylene.

7. The compound of claim 1 wherein R is isopropyl, $R^1$ is methyl and $R^1$ is phenyl.

8. The method of controlling undesirable vegetation comprising applying to the area where control is desired an herbicidally effective amount of a compound having the structural formula

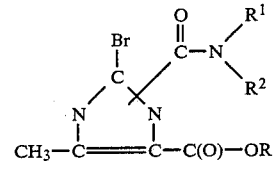

wherein R is $C_1$-$C_{10}$ alkyl, $C_3$-$C_8$ cycloalkyl, $C_3$-$C_8$ cycloalkylalkyl wherein the alkyl has 1 to 6 carbon atoms, $C_3$-$C_{10}$ alkenyl, $C_5$-$C_8$ cycloalkenyl; benzyl or mono- or di-substituted benzyl wherein the substituents are $C_1$-$C_4$ alkyl, halogen, nitro or $C_1$-$C_4$ haloalkyl; $R^1$ and $R^2$ independently are $C_1$-$C_6$ alkyl or phenyl; or $R^1$ and $R^2$ together from a saturated ring with the nitrogen to which they are attached having 3-8 carbon atoms, optionally substituted with one or two methyl groups.

9. The method of claim 8 wherein R is $C_3$-$C_5$ alkyl $R^1$ is $C_1$-$C_4$ alkyl and $R^2$ is $C_1$-$C_4$ alkyl.

10. The method of claim 8 wherein R is isopropyl, $R^1$ is methyl and $R^2$ is methyl.

11. The method of claim 8 wherein R is isopropyl, $R^1$ is methyl and $R^2$ is methyl.

12. The method of claim 8 wherein R is isopropyl, $R^1$ is isobutyl and $R^2$ is isobutyl.

13. The method of claim 8 wherein R is isopropyl, $R^1$ and $R^2$ together are butylene.

14. The method of claim 8 wherien R is isopropyl, $R^1$ is methyl and $R^2$ is phenyl.

* * * * *